US006819247B2

(12) United States Patent
Birnbach et al.

(10) Patent No.: US 6,819,247 B2
(45) Date of Patent: Nov. 16, 2004

(54) APPARATUS, METHOD, AND SYSTEM FOR REMOTE MONITORING OF NEED FOR ASSISTANCE BASED ON CHANGE IN VELOCITY

(75) Inventors: Jeffrey M. Birnbach, Sarasota, FL (US); Serge D. Jorgensen, Sarasota, FL (US)

(73) Assignee: Locast Corporation, Sarasota, FL (US)

( * ) Notice: Subject to any disclaimer, the term of this patent is extended or adjusted under 35 U.S.C. 154(b) by 381 days.

(21) Appl. No.: 09/785,649

(22) Filed: Feb. 16, 2001

(65) Prior Publication Data

US 2002/0116080 A1 Aug. 22, 2002

(51) Int. Cl.[7] .............................................. G08B 23/00

(52) U.S. Cl. ............................. 340/573.1; 340/573.7; 340/539.11; 340/539.13; 340/539.16

(58) Field of Search ...................... 340/573.1, 573.7, 340/573.4, 539.1, 539.11, 539.12, 539.13, 539.16, 539.17, 539.24

(56) References Cited

U.S. PATENT DOCUMENTS

| 4,670,739 A | 6/1987 | Kelly, Jr. |
| 4,844,091 A | 7/1989 | Bellak |
| 4,952,928 A | 8/1990 | Carroll et al. |
| 5,043,736 A | 8/1991 | Darnell et al. |

(List continued on next page.)

OTHER PUBLICATIONS (8) NERAC Citations from DTIC: DOD; (1) Konigsberg, EPH; Chemical Defense User Safety System; Konigsberg Instruments, Inc., Pasadena, Ca.;Doc. Order # AD–A319–616; Final rept. 03/86–06/91 Unclassified; (2) N. I. Klyadin, P. G. Kuznetsov, V. A. Lemenkov, M. D. Khodyreva; Biomedical Engineering (Journal); Copyright 2000 Elsevier Science B.V., Amsterdam; Dtd. 1999; 7 pgs. Dtd Jul. 19, 2000, including data and some abstract information; (3) Citations from EMBASW: EMB; K. J. Samson; 'Smart' shirt is first wearable medical monitor; Biomedical Instrumentation and Technology (Journal); Copyright 1999 Elsevier Science B. V., Amsterdam; Dtd. 1999; (4) Citations from INSPEC: INS; P. Konoske, W. Deniston, R. Barker, D. Moses; Evaluation of Mobile Medical Monitor (M#) in a field environment (Conference paper); Proceedings Pacific Medical Technology Symposium–PACMEDTek, Trancending Time, Distance and Structural Barriers; (Cat. No. 98EX211); Dtd. 1998.

(List continued on next page.)

Primary Examiner—Toan N. Pham
(74) Attorney, Agent, or Firm—McKee, Voorhees & Sease, P.L.C.

(57) ABSTRACT

The present invention is an apparatus, method, and system for remote monitoring of need for assistance based on change in velocity. One aspect of the invention includes a portable unit that may be comfortably wearable, having an intelligent control, and a detector capable of detecting a physical parameter related to acceleration, and a transmitter. When an acceleration is determined to exceed a particular threshold, the intelligent control device instructs a transmitter to send an alert signal. Another aspect of the invention includes a method of monitoring for need of assistance by monitoring a physical parameter of the person related to acceleration and transmitting a need of assistance alert. Another aspect of the invention involves a system including one or more monitor units for determining the need for assistance based on physical parameter related to acceleration, a communications network for receiving information from the monitored unit and notifying a third party.

109 Claims, 9 Drawing Sheets

U.S. PATENT DOCUMENTS

| | | | |
|---|---|---|---|
| 5,331,549 A | | 7/1994 | Crawford, Jr. |
| 5,365,217 A | | 11/1994 | Toner |
| 5,417,222 A | | 5/1995 | Dempsey et al. |
| 5,523,742 A | * | 6/1996 | Simkins et al. .......... 340/573.1 |
| 5,541,579 A | * | 7/1996 | Kiernan .................... 340/573.1 |
| 5,652,570 A | | 7/1997 | Lepkofker |
| 5,720,770 A | | 2/1998 | Nappholz et al. |
| 5,738,102 A | | 4/1998 | Lemelson |
| 5,771,001 A | | 6/1998 | Cobb |
| 5,883,576 A | | 3/1999 | De La Huerga |
| 6,095,991 A | * | 8/2000 | Krausman et al. .......... 600/595 |
| 6,144,314 A | * | 11/2000 | Yasue ......................... 340/7.1 |
| 6,166,656 A | | 12/2000 | Okada et al. |
| 6,287,252 B1 | | 9/2001 | Lugo |
| 6,302,844 B1 | | 10/2001 | Walker et al. |
| 6,307,481 B1 | * | 10/2001 | Lehrman et al. ............ 340/669 |
| 6,315,719 B1 | | 11/2001 | Rode et al. |
| 6,509,830 B1 | * | 1/2003 | Elliott ................... 340/286.02 |

OTHER PUBLICATIONS (5) Citations from NASA STAR: NAS; W. R. Dyck; A. Nicols; An Integrated Medical Monitor for Aeromedical Use (Conference Paper); Defense and Civil Inst. Of Environmental Medicine, Foreign Government, Operational Human Engineering Group, North York, Ontario Canada; (6) Citations form U.S. Patent Bibliographic Database: PA 1; John M. Crawford, Jr.; Medical monitor system; Pat. 5,331,549; Dtd. Jul. 19, 1994; (7) Citations from Patent Abstracts of Japan: PJ1, Kazunari Owada, Terumi Matsubara, Kazuo Matsubara; Medical Monitor and Display Device; 06292658 JP; Dtd. Oct. 1, 1994; (8) Citations from USG/NTIS; USG; W. M. Deniston, P. J. Konoske; W. M. Pugh; Mobile Medical Monitoring at Forward Areas of Care (Interim rept. for Jun 97); Rpt. #–NAVHLTHSCHC–98–18; Naval Health Research Center, San Diego, CA.

* cited by examiner

User I.D. : XXXXXXXXXXX
Name    : XXXXXXXXXXX

Notify:

| Name 1 | | Name 2 | | Name 3 | |
|---|---|---|---|---|---|
| Phone 1 | ☒ | Phone 2 | ☒ | Phone 3 | ☒ |
| E-mail 1 | ☐ | E-mail 2 | ☒ | E-mail 3 | ☒ |
| Pager 1 | ☐ | Pager 2 | ☐ | Pager 3 | ☒ |

Notify Emergency Responders ☒

*FIG. 9*

APPARATUS, METHOD, AND SYSTEM FOR REMOTE MONITORING OF NEED FOR ASSISTANCE BASED ON CHANGE IN VELOCITY

INCORPORATION BY REFERENCE

Co-owned, co-pending U.S. Ser. No. 09/666,732, filed Sep. 20, 2000, is incorporated by reference herein in its entirety.

FIELD OF THE INVENTION

The invention is an apparatus, method and system for providing remote monitoring of a person's need for assistance without necessarily monitoring physiological conditions at the person. More particularly, the invention monitors user spatial orientation, velocity and acceleration changes, and based on these changes, the invention determines if assistance may be required. The invention determines the location of the user and selectively communicates the location; orientation information obtained from the spatial orientation, velocity, and acceleration sensors; and the current alert status to a remote location.

PROBLEMS IN THE ART

There is an ever-growing number of people that engage in independent and/or active lifestyles but still may be susceptible to injury. Friends, family, loved ones, caretakers, caregivers, and other persons may not always be physically present to accompany or monitor the person. The friends, loved ones, caretakers, caregivers, and other persons may, however, want to be notified in case of any emergency situation involving the person susceptible to injury. One solution to this problem has been physiological monitoring. One example of physiological monitoring is the commonly owned application titled APPARATUS, METHOD AND SYSTEM FOR REMOTE MONITORING OF PHYSIOLOGICAL CONDITIONS, filed on Sep. 20, 2000 and having Ser. No. 09/666,732. In physiological monitoring, a person or user is connected to one or more physiological monitoring devices to monitor vital signs or other physiological information. Physiological monitoring has had numerous problems.

Typically, a physiological monitoring device senses physiological conditions of the user and immediately transmits these conditions to another location which remotely processes the information. Problems are present in the communication link from the device on a user to the central location. Some problems are related to the amount of physiological data that is sent. In order to properly monitor the vital signs or other physiological information of the user, frequent or continuous transmissions must be made. These transmissions may consume more bandwidth and more power than is desirable.

Another related problem concerning physiological monitoring devices involves the integrity of the information received over the communication link. Particularly where there is a large amount of information being transmitted in the process, there is the opportunity for this information to be corrupted. Where physiological information is corrupted in the transmission process, the goal of monitoring for emergency events and conditions is not fulfilled.

In addition, there is a security or privacy problem associated with transmission of physiological information. Users are not particularly amenable to having their physiological information capable of being monitored by third parties. Although these problems may be addressed through some extent through error checking and encryption, attempts at solving these problems may increase the bandwidth, or otherwise increase the overall complexity and cost of the device.

Another related problem is that these continuous transmissions of physiological data require additional power requirements that may make it infeasible for a battery operated device or else may result in a device that is large or cumbersome or requires frequent battery replacement.

In addition, the remote processing of this information may take considerable time. If there is a medical emergency, this must be known as soon as possible so that there is adequate time to respond to the emergency.

A further problem is that even when the physiological conditions of a user are monitored, the location of the user needs to also be known so that medical assistance can find the user if required.

Yet, another problem with physiological monitoring is that physiological monitoring requires a complex device such as with multiple sensors attached to the users body and other inherent constraints in current designs. These constraints make physiological monitoring inconvenient, uncomfortable and undesirable for users. In addition, these extra sensors may require design complexity that increases the overall size of the device. A larger, heavier device is also inconvenient for users to wear.

Another problem with physiological monitoring involves false alerts due to inaccurate monitoring. Physiological sensors may become displaced or detached from the body area they are monitoring. This results in the transmitted physiological readings not being reflective of the actual physiological condition of the user. Those monitoring the physiological conditions may only know the physiological readings and not realize that the sensors are simply not properly attached. This may result in false alerts.

These and other problems have made remote monitoring of people cumbersome, inconvenient, or sometimes unworkable.

OBJECTIVES, FEATURES, OR ADVANTAGES OF THE PRESENT INVENTION

It is therefore a primary objective, feature, or advantage of the present invention to provide an apparatus, method, and system which improve upon the state of the art.

It is another objective, feature, or advantage of the present invention to provide a system and method of user monitoring capable of alerting the desired response personnel.

Yet another objective, feature, or advantage of the present invention is to provide a monitoring device that may be comfortably worn.

It is a further objective, feature, or advantage of the present invention to provide a means of communicating alert information to emergency or health care professionals.

It is yet another objective, feature or advantage of the present invention to provide a monitoring device that is relatively simple in operation.

It is yet another objective, feature or advantage of the present invention to provide a remote monitoring device that requires only limited bandwidth.

It is yet another objective, feature or advantage of the present invention to provide a monitoring device that does not require any sensing devices, electrodes, tools, or equipment to be placed in direct contact with the user's skin.

It is yet another objective, feature, or advantage of the present invention to provide a monitoring device that is capable of onboard computations, monitoring, and decision making.

It is a further objective, feature, or advantage of the present device to provide an optional means of tracking the location of a person using the device, and communicate their location to medical care responders or other care providers.

It is yet another objective, feature, or advantage of the invention to optionally use the location-tracking device to provide data on the position and state, velocity, or acceleration of a person.

It is a further objective, feature, or advantage of the present device to provide an optional means of alerting nearby persons to the situation, and to attract the attention of rescue personnel upon their arrival.

It is a further objective, feature, or advantage of the present invention to provide information for updating notification information through a web-based interface.

It is a still further objective, feature, or advantage of the present invention to provide a system that may be cheaper, more durable, and more reliable than physiological monitoring.

It is a still further objective, feature, or advantage of the present invention to provide a method, system, and apparatus for remote user monitoring with reduced likelihood of false alerts.

It is a still further objective, feature, or advantage of the present invention to provide a means of transmitting information that need not be continuous and may be transmitted in a burst transfer.

These and other objectives, features, or advantages of the present invention will become apparent from the specification and claims.

SUMMARY OF THE INVENTION

The invention is a monitor unit that monitors a human body as a unit of mass including velocity, velocity changes, and other physical status and orientation information. The monitor unit is designed to be worn close to the body and may be worn on a person's clothing, such as on a belt, or placed in a pocket. The monitor unit determines whether there is a need for assistance based upon movement changes. These movement changes may be changes in velocity, changes in position, or acceleration.

The monitor unit is capable of communicating the need for assistance to a communications network, capable of notifying third parties of the need for assistance. The monitoring unit may also include a geographic location device so that location information may also be transmitted to a communications network so that a third party receives location information as well. The monitoring unit may also include an optional deactivation switch so that if there is no emergency, the person wearing the device can prevent a need for assistance alert from being sent. In addition, the sensitivity of the device may be set according to the needs of a particular person.

The invention also provides for a method of determining whether there is a need for assistance based on the movement changes sensed by the device.

The invention also provides for a system that includes a communication network and central control or directly to a selected person's telephone, pacer or other communication device. The communication network is capable of receiving transmitted signals from the monitor unit. The communication network may be a paging network, a cellular telephone network, a satellite network, a radio communications network, or other network. The communication network can then forward any need for assistance messages to a central control or directly to a selected person's telephone, pager, or other communication device. The central control can then process this information as needed and issue notification messages to users by telephone, pager, or electronic messaging.

BRIEF DESCRIPTION OF THE DRAWINGS

FIG. 9 is a diagram of a user interface that permits a user to modify contact information for people who are notified.

DETAILED DESCRIPTION OF AN EXEMPLARY EMBODIMENT

Overview

Figure 1:
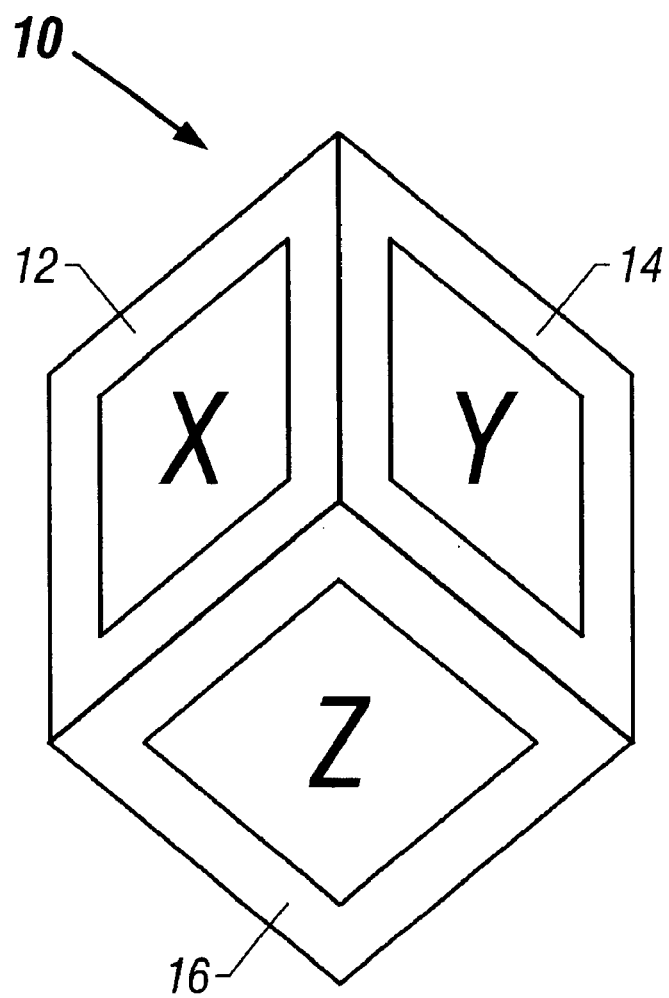
FIG. 1 is a diagrammatic representation of an accelerometer having three axes such as may be used in an exemplary embodiment.

For a better understanding of the invention, an exemplary embodiment will now be described in detail. Frequent reference will be taken to the drawings. Reference numerals and letters will be used in the drawings to indicate certain parts and locations in the drawings. The same reference numerals or letters will indicate the same parts or locations throughout the drawings unless otherwise indicated.

Apparatus of Exemplary Embodiment

FIG. 1 is a diagram showing an accelerometer 10 that may record readings in 3 axes over a range of g forces. In a three-axis accelerometer, as shown, measurements are made over the X dimension 12, the Y dimension 14, and the Z dimension 16. The present invention contemplates, that if need be, multiple one axis or two axis accelerometers may be used (the accelerometers oriented on different planes) such that acceleration may be measured with respect to all three axes. One example of a type of accelerometer that may be used is the IMEMS ADXL210, which is available from Analog Devices. The criteria for the device includes size, power consumption, and impact measurement range and accuracy. Accelerometers that are smaller in size, have reduced power consumption, and have increased impact measurement range and increased measurement accuracy are preferred. For example, an accelerometer may have an impact measurement range that is less than or equal to 10 g's, and may have an accuracy of 10 mg's or less.

Figure 2:
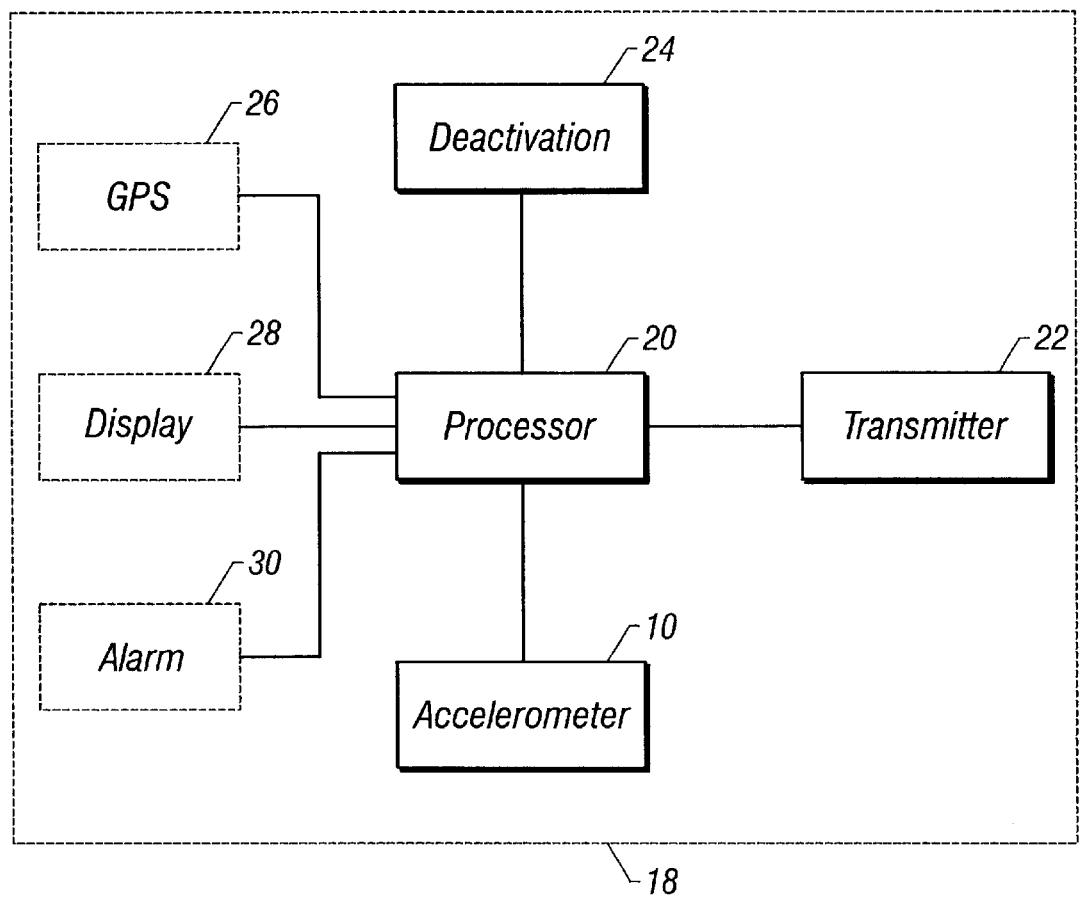
FIG. 2 is a block diagram of the monitor unit according to one embodiment.

FIG. 2 illustrates that accelerometer 10 is a part of a user monitor 18. The accelerometer 10 is electrically connected to a processor 20. The specific interface between processor 20 and accelerometer 10 is dependent upon the specific processor 20 and the specific accelerometer 10 used. The present invention contemplates that this interface may be through a standard RS-232 serial communication; proprietary interfaces; I$^2$C, SPI or other bus interfaces. Similarly, digital outputs of the accelerometer 10 may be connected to digital inputs on the processor 20 and that digital inputs to the accelerometer, if any, may be connected to digital outputs on the processor 20.

The present invention also recognizes that sensors other than accelerometers may be used, that sense information that can be used to calculate impact. Other devices that sense acceleration or other velocity shift measurement devices may be used. Such alternate measurement devices may include a more accurate GPS system or other location determining system.

The processor 20 may be a standard RISC-133 processor, though many other intelligent devices are contemplated by this invention. The present invention is not limited to a particular type of processor. Preferably the processor used is small, lightweight, and has low power consumption. In addition to a processor, other intelligent control devices may be used. The present invention contemplates that a processor, microprocessor, microcontroller, digital signal processor, integrated circuit, or portion of an integrated circuit may also be used. The intelligence of the device may be implemented in hardware, software, or a combination thereof.

The processor 20 is also electrically connected to transmitter 22. Transmitter 22 is capable of transmitting information, such as alert messages that will be discussed later in detail, from the processor to a remote location. The transmitter 22 may be a transmitter such as used in pager. The transmitter 22 may be either a one-way pager or a two-way pager such as may be used with the SKYTEL network or pager network. The transmitter 22 may use any number of standard paging protocols such as the MOTOROLA REFLEX protocol. The present invention contemplates that the type of network used and the corresponding transmitter need not be a paging unit, but could be a cellular network using CDPD or other technology, a satellite network, or other type of wireless network such as may be known in the art. The type of transmitter 22 is selected based on considerations of low power requirements, safe close-proximity transmission, and adequate structure penetration. The messages sent over the communication channel can be small and simple binary strings as will be explained.

A deactivation means 24 is also shown in FIG. 2. Deactivation means 24 is electrically connected to processor 20. The deactivation means 24 may be a button or other switch that serves as a user input to the processor. The purpose of deactivation means 24 is to provide the user of the device 18 with a method of preventing an alert from occurring. The purpose of the deactivation means 24 will become even clearer in later discussion of the invention.

FIG. 2 also shows the optional use of GPS unit 26, display 28, and alarm 30. These components may all be connected to processor 20 in the manner suggested by the particular GPS unit 26, display 28, and alarm 30 used.

The GPS unit 26 may communicate with processor 20 through proprietary messaging associated with a particular GPS unit 26 over a proprietary interface associated with the particular GPS unit 26. Alternatively, the GPS unit 26 can communicate with the processor 20 through an RS-232 interface (for signaling purposes, but voltage level may be 5V or other standard) using the standard NMEA protocol such as is well known in the art. The GPS unit 26 may be an embedded chip such as is available from Garmin and other manufacturers.

A display 28 is another option of the monitoring device 18. The device provides its wearer with a visual indication of whether an alert has successfully been sent and received or whether or not monitor unit 18 has successfully been deactivated. The present invention contemplates that other information may be displayed on display 28 as may be convenient for the user of device 18.

The optional alarm 30 is also electrically connected to processor 20. The alarm may be a loud audible alarm so to draw the attention of others when activated. The present invention contemplates that the alarm may also be visual in nature, such as a flashing light, or other indicator of an emergency situation.

If CPDP, cellular, or other voice communication networks are used, the present invention contemplates that the device may also include a voice construction component. The voice construction component may be implemented through software in the processor, or may be implemented with an integrated circuit, or portion of an integrated circuit.

The monitor unit may also include an optional sensitivity settings that may be selected through dipswitches or may be programmed. Different users will require different sensitivity settings. For example, a 90 year old man may require greater sensitivity to changes in velocity or acceleration than a 13 year old boy. Age, size, and condition as well as other factors may be taken into account when determining the proper setting for sensitivity.

As the invention monitors the status of the body as a unit of mass, preferably the monitor unit 18 is placed at or close to the center of mass for an individual. Preferably, the monitor unit 18 is snug with a location such as in the trunk or torso and not an arm or leg.

System of an Exemplary Embodiment

Figure 3:
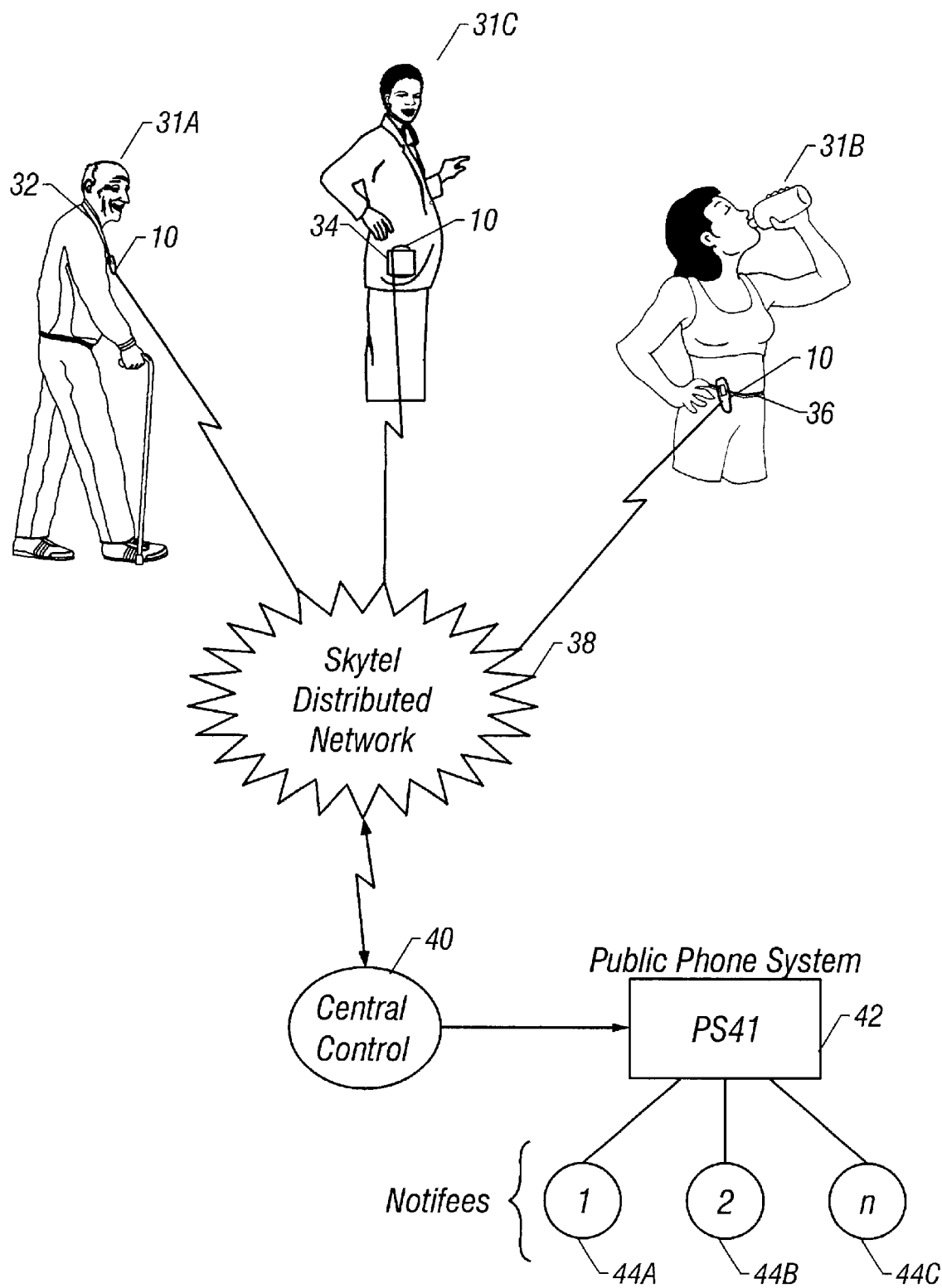
FIG. 3 is a pictorial representation of the system of the present invention permitting third parties to receive alerts concerning monitored persons.

FIG. 3 is a diagrammatic representation of the system of the present invention. In FIG. 3, users 31 each carry the monitor unit 10. User 31A carries the monitor unit 10 on a strap 32 capable of being worn around the neck. User 31B carries the monitor unit 10 on a belt 36. User 31C carries the monitor unit 10 in pocket 34. The monitor unit 10 is in communication with a distributed network such as SKYTEL 38. The distributed network SKYTEL 38 is in communication with a central control 40. This communication between SKYTEL 38 and central control 40 may be through an Internet connection such as is known in the art. For example, electronic messages may be sent from a pager over SKYTEL to an Internet email address.

Central control 40 is also connected to the public telephone system 42. Central control 40 can then forward messages to those who are to be notified 44 through the public telephone system 42. The present invention permits central control 40 to notify the persons to be notified 44 through other means such as through electronic email or through paging.

Exemplary Method of the Present Invention

Figure 4:
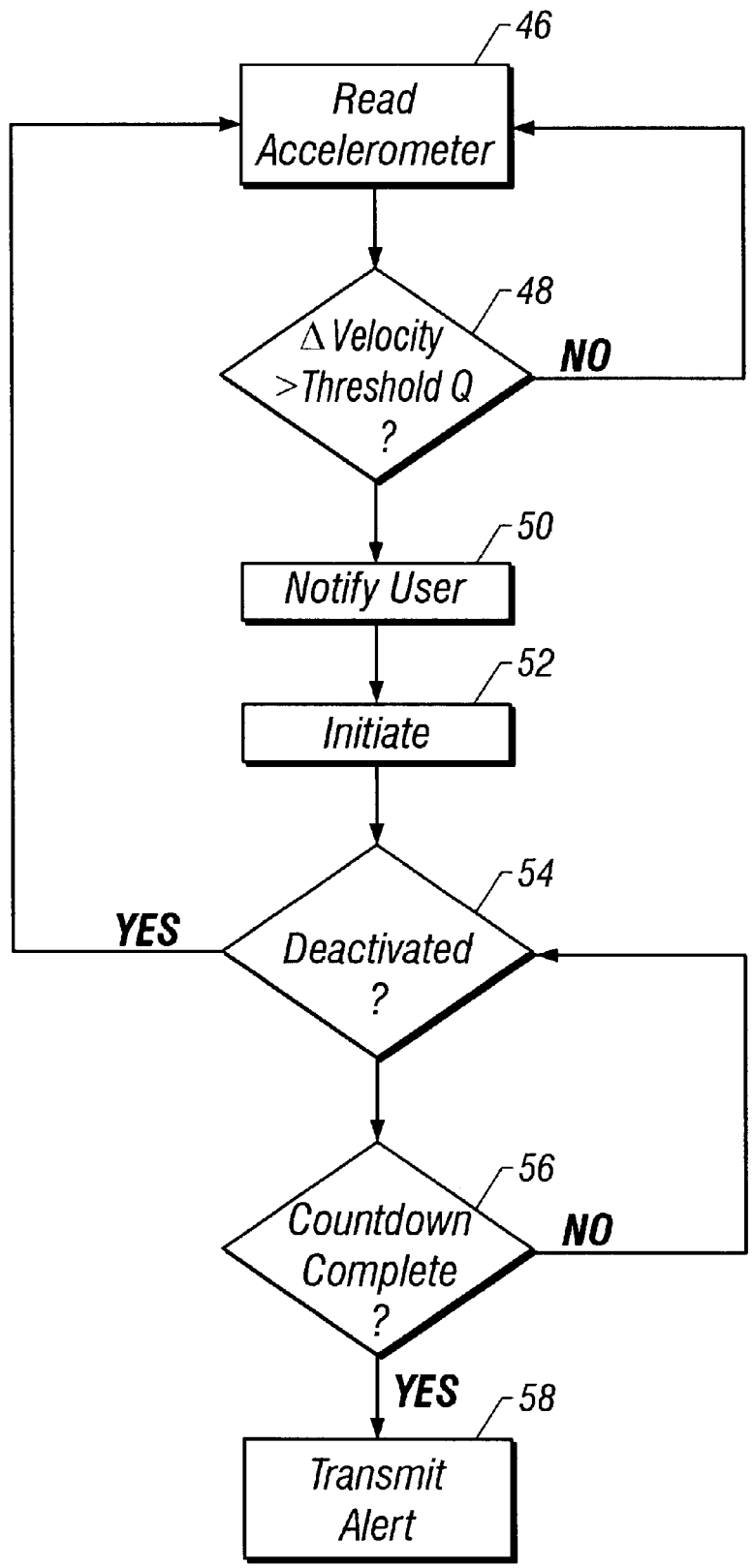
FIG. 4 is a flow diagram illustrating one embodiment of the notification process of the present invention.

FIG. 4 illustrates the logical flow of one embodiment of the method of the invention. In step 46, an accelerometer output an acceleration reading or an acceleration or velocity change reading is otherwise calculated. The accelerometer reading is then compared to a threshold Q in step 48. Q is a threshold selected for the particular user of the device. The threshold is selected on the basis of physical size of the person as well as the condition of the user. The greater the Q the higher the force that the person wearing the device is expected to be able to withstand without harm. If the measured acceleration is not greater than Q, then the accelerometer is read again in step 46. If the acceleration is greater than the Q threshold, then in step 50, the user is notified. This notification can be accomplished through the use of the display 28 or the alarm 30, or other means such as would be convenient. Once the user is notified in step 50, a countdown is initiated in step 52. The countdown relates to a set period of time during which the user may deactivate the alarm. If the countdown is completed without deactivation, then an alert is transmitted. As step 54 shows, a determination is made as to whether the alarm is deactivated. If the user does deactivate the alarm such as through pressing of a button or switch, then there is no alert transmitted and the acceleration is read again in step 46. If there is no deactivation, then in step 56 a determination is made as to whether the countdown is complete. The time of the countdown is selected based upon the particular user of the device and the amount of time reasonably necessary to ensure that if the user is not injured, the user will have time to press a button or otherwise deactivate the device prior to any alert being transmitted. This amount of time is selected based upon the physical condition of the user, the type of deactivation means used, how the monitor unit 18 is typically worn, and other considerations related to the amount of time the user may require for deactivation. If the countdown is not complete, then in step 56, the processor again determines whether the alert has been deactivated in step 54. If the countdown is complete in step 56, then in step 58 an alert is transmitted.

Figure 5:
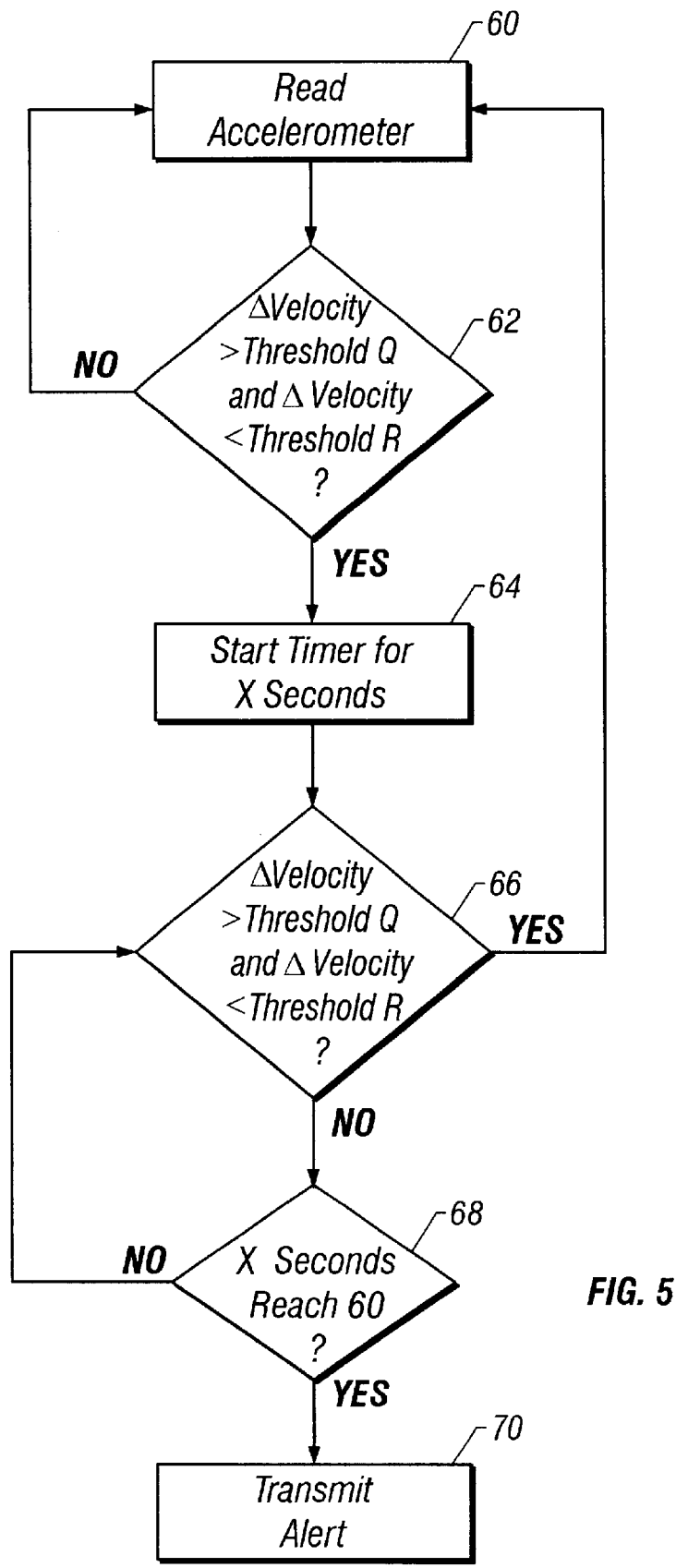
FIG. 5 is a flow diagram illustrating one embodiment of the processing of acceleration information.

FIG. 5 illustrates another embodiment of the present invention. This embodiment permits an alert to be transmitted only when an acceleration reading has been at a particular level, defined as between the threshold Q and the threshold R, only once during a particular amount of time, X. This embodiment is useful in that it can be used to eliminate false triggering that may occur when a person wearing a monitor unit 10 travels in a car or other vehicle, thus experiences acceleration unrelated to the physical condition of the person. In addition, this embodiment is useful in that if there is additional acceleration after time X, it is apparent that the person is not in medical danger and no alert need be transmitted. For example, a person could fall and then get up on their own, thus there would be no need for an alert.

In FIG. 5, step 60, the accelerometer is read. Then in step 62 a determination is made as to whether the acceleration is greater than the threshold Q and the acceleration is lower than a threshold R. If the acceleration is not greater than the threshold Q and the acceleration is less than a threshold R then in step 64 a timer is started for X seconds. In step 66, another determination is made as to whether the acceleration is greater than the threshold Q and the acceleration is lower than a threshold R. If so, then no alert is transmitted, and the accelerometer is read again in step 60. If not, then in step 68 a determination is made as to whether the X seconds have elapsed in step 68. If not, then the process returns to step 66 and another determination is made as to whether the acceleration is greater than the threshold Q and the acceleration is lower than a threshold R. If X seconds have elapsed, then in step 70, an alert is transmitted.

Figure 6:
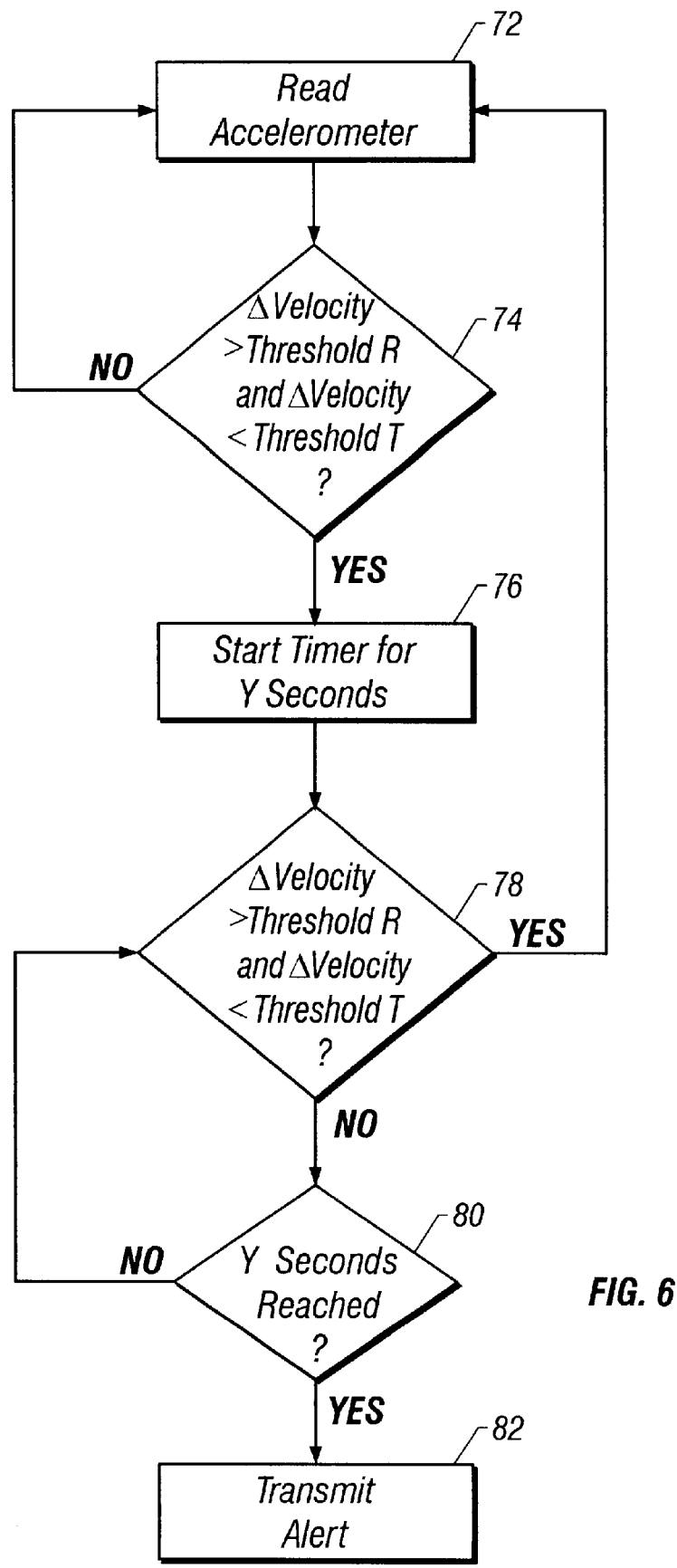
FIG. 6 is a flow diagram illustrating another embodiment of the processing of acceleration information.

FIG. 6 illustrates another embodiment of the present invention. FIG. 6 is similar to FIG. 5, except for instead of the acceleration being compared to the range between Q and R, the acceleration is being compared to the range between R and T. In addition, instead of the timer being set for X seconds as in FIG. 5, the timer is set for Y seconds.

It should be apparent to one skilled in the art that multiple embodiments may be combined and used together. For example, if the acceleration is over a first value, then an alert is transmitted (after opportunity for deactivation). This setting would cover those instances of great acceleration where it is clear that a person may be endangered from the level of the acceleration. In addition, the acceleration could be compared to a second range. When the acceleration is in this range only once in X amount of time, the person may be endangered. In addition, the acceleration could be compared to a third range. When the acceleration is in this third range only once in Y amount of time, the person may be endangered.

It should be apparent that this method of comparing accelerometer thresholds and timing the occurrences of accelerometer readings that are greater than or less than these thresholds permits alerts to be transmitted that relate to the amount of force that the person wearing the accelerometer is experiencing. The amount of force is related to the presence or absence of an alert condition.

The present invention also contemplates more complex methods of operation concerning the transformation of sensed accelerometer readings into indications of the need for assistance.

The present invention contemplates that the acceleration readings may be sampled at any number of rates. However, the present invention also recognizes that by reducing the number of accelerometer readings required, the power consumption of the monitor unit 18 is reduced, thus extending battery life. The present invention also recognizes that the accelerometer may sample and communicate those samples to the processor faster than is required to monitor a person. The frequency of sampling is also related to the velocity at which the person is moving. The higher the velocity, the greater the need for more frequent sampling so as to ensure more accurate calculations of acceleration. The present invention contemplates that for many applications, sampling need not be greater in frequency than 5 times per second. However, higher sampling rates may be used.

Figure 7:
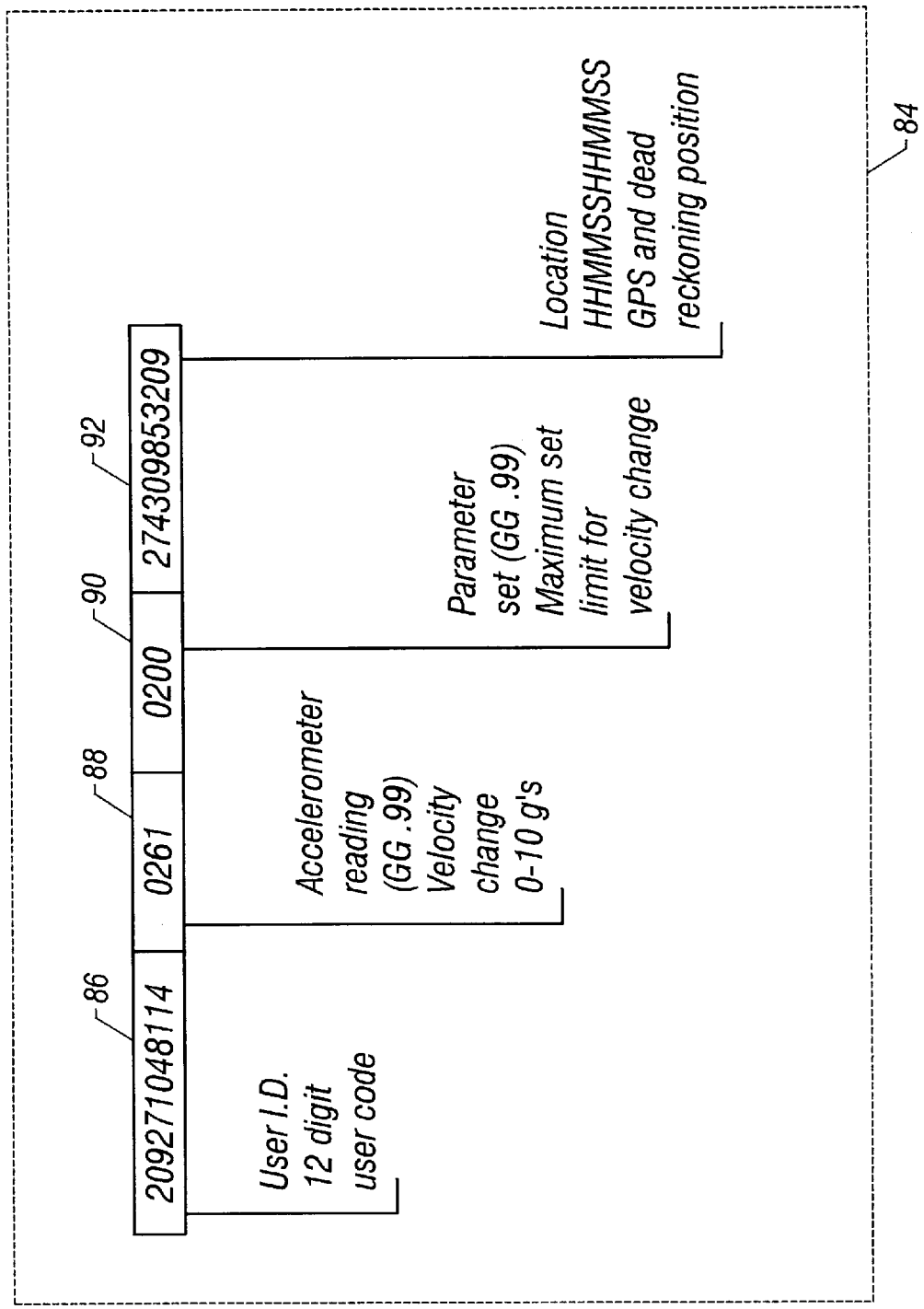
FIG. 7 is a diagram showing an exemplary message from the monitor unit.

FIG. 7 shows a message 84 having a user ID 86, an accelerometer reading 88, a parameter 90, and a latitude/longitude 92. The user ID 86 may be a 12-digit code. The accelerometer reading 88 may be a five significant digit number representing an accelerometer reading between 0 and 10 g's and the direction of acceleration. For example, one accelerometer reading may be 2.61 g. The parameter 90 may also be a four significant digit number between 0 and 10 g's representing the threshold that has been exceeded. For example, one threshold may be 2.00 g. When the acceleration exceeds the parameter, both the parameter and the threshold may be sent. The parameter may be necessary to communicate which type of event detection was used when a device supports multiple methods of detection. The latitude/longitude 92 provides a location, such as from a GPS. The latitude and longitude provide the hours, minutes, and seconds associated with the current (or last known) location of the monitor 18. The present invention is in no way limited by the particular message being sent as the present invention contemplates numerous variations on the message to indicate that an alert should be issued.

The user can assign the party to be notified. The user can select to notify a loved one instead of emergency officials or a call center. The loved one receives a phone call and hears a message relaying the location, nearest major intersection, and amount of parameter violation in lay terms. Suitable action can then be taken.

FIG. 9 is a representation of a web based user interface of the present invention. In FIG. 9, a user is provided the ability to select the people who are to be notified in case of an emergency. Through use of web based interface, user may add, change, or delete the name of the person to be notified in case of there being a need for assistance. In addition, a user can modify the information associated with each name, including the telephone number, the e-mail address, and the pager number associated with each person. In addition, the user can select that method of contact for that person, including the selection of multiple methods. Thus, for example, a person may be contacted via telephone, e-mail, and by pager.

Figure 8:
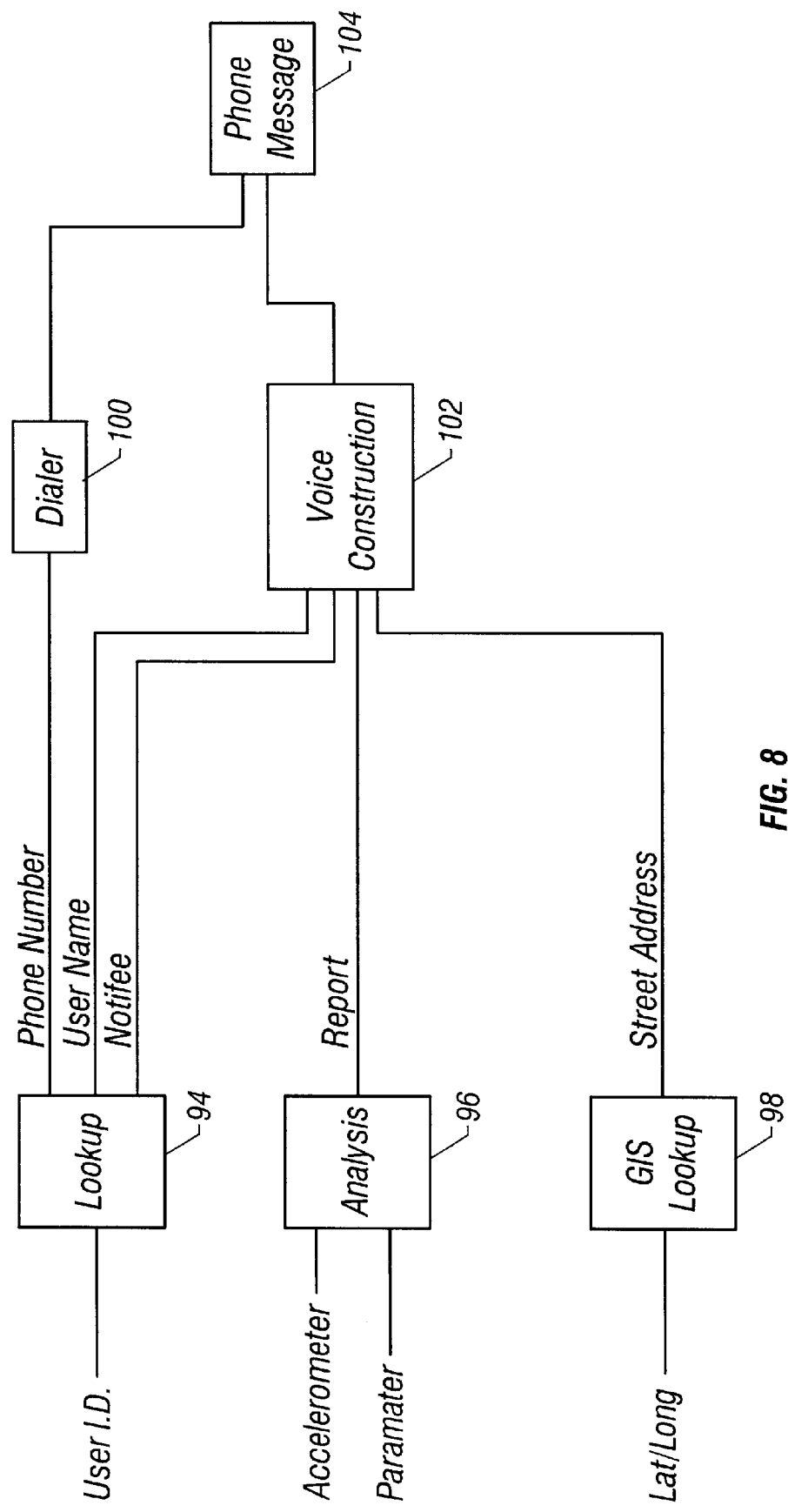
FIG. 8 is a diagram showing the flow of information from the monitor to those being notified of an alert.

FIG. 8 further illustrates the information flow in one embodiment of the present invention. In FIG. 8 certain information is transmitted from the monitor unit 18. This information may include a user ID, an accelerometer reading, a parameter that has been exceeded, and a latitude/longitude. This information is sent or forwarded to a central control from the SKYTEL network, or other paging system. For example, the information could be electronically mailed or otherwise sent to the central control such as is well known in the art. The information received from the monitor unit is used for different purposes. For example, the user ID is used to provide a lookup function 94. This lookup may be in a database, such as a relational database. Other information that may be associated with the user ID include the user's name, the identity of those who are to be notified, and telephone numbers and email addresses of those who are to be notified. The present invention contemplates that other information may also be associated with the user ID, such as information related to the health of the user.

The accelerometer reading and the threshold parameter information is used by an analysis function 96 of the present invention. The analysis function 96 can be used to provide additional analysis of the accelerometer information. The analysis function 96 can take into account other information as well, including the condition of the user as well as the location of the user, past injuries, past alerts, and other information such as may be useful in predicting more information concerning the meaning of the acceleration or acceleration change experienced by the user.

The latitude and longitude or other location information may be used by a geographical information systems (GIS) function 98 of the present invention. The GIS lookup function 98 can correlate a precise GPS location with a particular street address, nearest intersection, or other location information that is more descriptive to a person.

The present invention permits a person to be notified to be called. The present invention also contemplates that the person to be notified may be otherwise contacted such as by paging or through electronic mail or other electronic messaging. When a person is to be called, a dialer function 100 may be used to dial the telephone number associated with each person who is to be notified. A voice construction component 102 may be used to translate the information concerning the user's identity, location, and information concerning the problem into voice information communicated within the phone message 104. The voice construction component may be any number of text to voice applications used in telephony and other applications and such as are known in the art.

The present invention contemplates various other configurations and modes of operation. For example, monitor unit 18 of FIG. 2 may be combined with or otherwise used in conjunction with a device for physiological monitoring such as disclosed and apparatus, method and system for remote monitoring of physiological conditions, U.S. application Ser. No. 09/666,732, incorporated by reference herein. In this and other combinations contemplated by the present invention, transduced medical conditions such as blood pressure, heart rate, temperature, and other conditions would be monitored, in addition to the acceleration, change in velocity, or rather physical parameter related to the force.

In order to provide additional description of the present invention, step-by-step examples are now given for particular configurations, communications, and modes of operation of the present invention. It is to be understood, that these examples are in no way limiting. The present invention contemplates various other configurations, and modes of operation.

Monitoring of a Person Prone to Injury Upon Falling

For purposes of this example, a person is at risk of injury during a fall due to osteoporosis or similar disease. They wish to notify their loved ones, care providers or emergency officials in case of an accident in case they are incapacitated. The user, however, also maintains a healthy and active lifestyle, and often engages in early morning walks, golf, and other activities where they may alone for a length of time. While not at grave risk for medical problems, it is possible that the user becomes unable to move towards assistance and may be in areas where others would be unaware of their difficulty.

Rather than requiring invasive or restrictive monitoring devices that the user would rapidly tire of wearing, this unit would be simply attached to a belt, waistband, or other clothing item normally worn. This encourages the user to continue wearing the device and to include it as part of their daily lifestyle and regimen. This is important for the low-risk user that is yet capable of sustaining a disabling injury while away from areas frequented by other people and potential caregivers.

On board criteria is set to different parameters depending on the risk level of the user. In this case, a gentle fall that might leave a bruise on a more robust bone structure could result in a broken hip or leg; therefore the unit is programmed by the user to send an alert after a relatively low impact or change in velocity (acceleration). Velocity changes and settings can be based upon the age and height of the user, where on the body the unit is located, and the condition of the user. For example, a person may be at risk when exceeding a 2.00 g force.

Upon event occurrence, in this case, a fall of 2.61 g, the first notification is local to the user. This beep and countdown feature allows the users to deactivate the device with a button-push if they have fallen, dropped the device independently of their person, or otherwise activated the monitoring unit. If the device is not deactivated within a short time, a signal is generated as shown in FIG. 7.

The information sent includes the threshold parameter of 2.00 g. This indicates which threshold was exceeded. Based on the accelerometer reading and the threshold that was exceeded, further information concerning the event triggering the alert may be determined, or the event may be further categorized. For example, the event may be categorized as "a serious fall." In addition the location information corresponding to a latitude of 27° 43' 09" and a longitude of 85° 32' 09" seconds correlates to a specific street address and intersection. It is not necessary to transmit the entire location information such as east, west, north, south, where it is known that a person's activity will be limited in geographical scope.

Based upon the received information, a loved one or an emergency response unit may contacted. For example, a family member may be notified by telephone of who may have sustained an injury, where the person is, and some information concerning the severity of the injury based upon the force involved.

An apparatus, method, and system for remote monitoring of need for assistance based on change in velocity has been disclosed. It should be apparent to one skilled in the art that the present invention contemplates numerous variations in the type of communication system used, the type of sensor used, the message transmitted from the monitor unit, the message received by a person to be notified, the amount of analysis performed on the information received, the type and number of thresholds used, and other variations such as a particular use or environment may require or suggest. In addition, it should be apparent to one skilled in the art that the present invention may be combined with physiological monitoring devices.

What is claimed is:

1. An apparatus for monitoring movement of a human body as a unit of mass for possible need of assistance comprising:

a portable sized housing adapted to be hand carried, held in pocket, or removably attached to a user or user's clothing;

in the housing, a processor, a wireless transmitter operatively connected to the processor, a geographic location device operatively connected to the processor and capable of detecting geographic location of the apparatus, and a detector operatively connected to the processor, the detector detecting one or more of the group comprising motion, velocity, acceleration, orientation; the processor programmed to instruct the transmitter to send a signal upon detection of a certain type or types of movement of a user detected by the detector, the signal comprising a code from which possible need of assistance and geographic location can be derived.

2. The apparatus of claim 1 wherein the wireless transmitter further comprises a wireless transceiver.

3. The apparatus of claim 2 wherein the detection and instruction to the wireless transceiver are processed by the apparatus.

4. The apparatus of claim 1 wherein the processor is selected from the set comprising a microprocessor, a microcontroller, an integrated circuit, a portion of an integrated circuit, and an embedded computer.

5. The apparatus of claim 1 wherein the detector comprises an accelerometer.

6. The apparatus of claim 5 wherein the accelerometer does not need to have accuracy less than 10 mg's.

7. The apparatus of claim 5 wherein the detector detects changes in orientation or velocity of a mass.

8. The apparatus of claim 1 wherein the detector is a geographic position device.

9. The apparatus of claim 1 wherein the detector is a velocity shift measurement device.

10. The apparatus of claim 1 further comprising manually operable control on the housing adapted for operation by a user.

11. The apparatus of claim 10 wherein the control is adapted to create a signal through the processor to override a perceived need for assistance status.

12. The apparatus of claim 1 wherein said certain type or types of movement are indicative of need for assistance.

13. The apparatus of claim 1 wherein the signal occurs only upon meeting a certain condition programmed into the processor.

14. The apparatus of claim 13 wherein the certain condition is programmed by a switch setting.

15. The apparatus of claim 1 wherein said signal causes generation of an alarm.

16. The apparatus of claim 15 wherein the alarm is sent to a central control.

17. The apparatus of claim 16 wherein said central control generates a call to a third party.

18. The apparatus of claim 17 wherein said call comprises at least one of a telephone call, a page, an e-mail, a cellular network transmission, or a digital message.

19. The apparatus of claim 18 wherein the third party selected from the group comprising emergency personnel and one or more persons selected by the user.

20. A method of monitoring movement of a human body as a unit of mass for possible need of assistance comprising:

monitoring a physical parameter of a person comprising one or more of velocity, change in velocity, acceleration, change in position with a device carried on the person;

deriving geographic location of the person with a device carried on the person;

transmitting a signal if the physical parameter is indicative of need of assistance, the signal comprising a code from which possible need of assistance and geographic location can be derived.

21. The method of claim 20 wherein the physical parameter indicative of need of assistance is acceleration or change in position above a certain threshold.

22. The method of claim 20 further comprising transmitting the signal to a wide area communications network.

23. The method of claim 22 wherein the wide area communication network transmits a signal to one of a central control, a designated recipient, or the user.

24. The method of claim 20 wherein the monitoring of a physical parameter comprises a carrying a relatively small portable, hand sized or smaller device on the user.

25. The method of claim 20 further comprising monitoring a physical parameter of a plurality of persons.

26. The method of claim 25 further comprising a central control adapted to receive a signal from any of the users and iterate a responsive action.

27. The method of claim 26 wherein the responsive action can be one or more of turning a query to the user, notifying third party, transferring signal to another entity.

28. The method of claim 20 wherein transmission of signals is accomplished over a wide area communications network.

29. The method of claim 28 wherein the wide area communications network is a wireless paging system.

30. The method of claim 28 wherein the wide area network is a cellular network.

31. The method of claim 28 wherein the wide area network is a satellite based wide area communication network.

32. The method of claim 20 wherein the monitoring of a physical parameter comprises a programmable threshold related to the physical parameter.

33. A system for monitoring a human body as a unit of mass in order to detect possible need for assistance comprising:

one or more portable user devices each adapted to be worn or carried by a user, each device including a wireless transmitter and a monitor of position and change in position of the device and a monitor of geographic position of the device;

a wireless wide area communication network;

each device programmed to generate a transmission from the transmitter into the communication network upon detection of a condition indicative of a need for assistance by the monitor of the device, the transmission comprising a code from which possible need of assistance and geographic location can be derived.

34. The system of claim 33 wherein the monitor comprises a device selected from the group of an accelerometer, geographic position sensor, a velocity shift detector, and a gyro.

35. The system of claim 33 further comprising a central control operatively connected to the communication network.

36. The system of claim 35 wherein the central control includes a processor with programming to evaluate any transmission from the user device and take action based on one or more conditions.

37. The system of claim 36 wherein the actions are selected from the set comprising: sending a query tn the user, notifying third parties, notifying an emergency responder, notifying a third party via telephone, notifying a third party via pager, notifying a third party via an electronic message.

38. The system of claim 33 wherein the monitor is set to detect movement or lack of movement suggesting potential need for medical assistance.

39. An apparatus for monitoring the human body as a unit of mass comprising:
 a means for monitoring changes in velocity carried on or with the human body;
 a means for generating geographic position carried on or with the human body;
 a means to transmit a signal if a change in velocity indicative of potential need for assistance is sensed, the signal comprising a code from which possible need of assistance and geographic location can be derived.

40. An apparatus for monitoring a human body as a unit of mass in order to determine need of assistance, the apparatus comprising:
 an accelerometer carried on or with the human body for measuring changes in velocity associated with a human body, the accelerometer capable of outputting a signal representing measured changes in velocity;
 a geographic location device carried on or with the human body;
 an intelligent control for receiving the signal from the accelerometer and determining if the measured change is indicative of a need for assistance;
 a transmitter electrically connected to the intelligent control, the transmitter capable of sending a message to a remote location indicative of a need for assistance, the message comprising a code from which possible need of assistance and geographic location can be derived.

41. The apparatus of claim 40 further comprising a housing; the accelerometer, intelligent control, and transmitter contained in the housing, the housing capable of being worn close to the human body.

42. The apparatus of claim 40 further comprising a geographic location device, the geographic location device capable of determining the geographic location of the apparatus, the geographic location device electrically connected to the processor.

43. The apparatus of claim 40 further comprising a deactivation component, the deactivation component electrically connected to the processor, the deactivation component capable of sending a signal to the processor indicative that there is no need for assistance.

44. A system for monitoring a human body as a unit of mass in order to determine need of assistance, the system comprising:
 a monitor unit to be worn close to the human body, the monitor unit capable of measuring velocity changes, comparing the velocity changes to a threshold, and transmitting the measured velocity changes, the monitor unit further capable of determining a geographic location and transmitting the geographic location;
 a communications network for receiving code from which possible need of assistance based on measured velocity changes and geographic location from at least one monitor unit can be derived;
 a central control capable of receiving messages from the communications network, the communications network capable of forwarding code from which possible need of assistance based on measured velocity changes and geographic location from a monitor unit can be derived, the central control capable of forwarding to third parties a communication requesting assistance at the geographic location of the human body.

45. An apparatus for monitoring a human body as a unit of mass in order to determine need of assistance, the apparatus comprising:
 a means for detecting changes in velocity carried on or with the human body;
 a means for determining a need for assistance based on the detected changes in velocity;
 a means for generating geographic position carried on or with the human body;
 a means for transmitting a signal comprising a code containing information from which possible need of assistance and geographic position can be derived.

46. The apparatus of claim 45 further comprising a means for detecting geographic location.

47. A system for notifying third parties of a need for assistance of a human body based on changes of velocity of the human body comprising:
 a monitor unit having a means for detecting changes in velocity carried on or with the human body; a means for detecting changes in geographic position carried on or with the human body; a means for determining if changes in velocity indicate a need for assistance; and a means of transmitting a signal carrying a code containing information from which possible a need for assistance and geographic position can be derived;
 a communications network having a means for receiving the signal; and a means for forwarding the signal;
 a central control having a means of receiving the signal from the communications network; and a means of alerting a third party by telephone, pager, or electronic message of the need for assistance and geographic location.

48. An apparatus adapted for monitoring acceleration and deceleration of the user comprising:
 a sensor adapted to transduce the average acceleration of a user when operatively mounted on the user;
 a programmable processor operatively connected to the sensor;
 a transceiver operatively connected to the processor and/or sensor,
 a location sensing receiver operatively connected to the processor to provide location data;
 software operatively loaded on the memory of the processor and adapted to receive transduced information from the sensor, compare the transduced information to pre-defined parameters, and decide if any message should be transmitted in code form through the transceiver based on that comparison and containing geographic position of the sensor.

49. The apparatus of claim 48 further comprising a mounting system to allow the user to removably mount the apparatus to the user, and where the apparatus does not require or rely on any invasive attachment or direct connection to the user.

50. The apparatus of claim 49 wherein the mounting system comprises an adjustable strap.

51. The apparatus of claim 49 wherein the mounting system comprises an adhesive.

52. The apparatus of claim 49 wherein the mounting system comprises a clip or similar attachment to clothing or other wearable items.

53. The apparatus of claim 48 wherein the sensor comprises an accelerometer.

54. The apparatus of claim 48 wherein the sensor comprises some other device measuring change in velocity.

55. The apparatus of claim 48 further comprising a housing sized for wearability by the user and which is mounted to the sensor.

56. The apparatus of claim 55 further comprising mounting the processor and transceiver in the housing.

57. The apparatus of claim 48 wherein the transceiver transmits and receives radio energy waves.

58. The apparatus of claim 48 wherein the parameters include thresholds.

59. The apparatus of claim 58 wherein the thresholds have a value that if exceeded, triggers a reportable event.

60. The apparatus of claim 58 wherein a reportable event triggers a transmission by the transceiver.

61. The apparatus of claim 60 wherein the transmission comprises a code.

62. The apparatus of claim 61 wherein the code is correlated to a physiological condition of the user.

63. The apparatus of claim 60 wherein the transmission only occurs on request or on a reportable event.

64. The apparatus of claim 48 further comprising a processing center including a second transceiver adapted for communication with said transceiver associated with said sensor.

65. The apparatus of claim 48 further comprising a geographical location device.

66. The apparatus of claim 65 wherein the geographical location device comprises a global positioning system receiver.

67. The apparatus of claim 65 wherein the geographical location device comprises a triangulation processor.

68. The apparatus of claim 65 wherein said geographic device is operatively connected to at least one of the processor and transceiver.

69. The apparatus of claim 65 wherein both comparison of the transduced information to the parameters and location of a user are generated and available for transmission by the transceiver.

70. The apparatus of claim 48 further comprising a manually operable component adapted to generate a transmission by the transceiver if so chooses the user.

71. The apparatus of claim 48 further comprising a second such apparatus independently programmed, both first and second apparatus adapted to communicate with a processing center transceiver.

72. The apparatus of claim 71 wherein said processing center transceiver is adapted to generate a response to a transmission by the transceiver of the apparatus, the response comprising generation of a signal to a third party.

73. A method for remote monitoring of an accelerated state of a user comprising the steps of:
    transducing information related to this state at or near the location of the state;
    comparing the transduced information to pre-determined criteria at or near the location of the state;
    monitoring further motion or states of the user and comparing this to expected values;
    transducing geographic location of the state;
    transmitting code if indicated by the comparison, the code comprising information from which possible need of assistance and geographic location can be derived.

74. The method of claim 73 wherein said step of transducing comprises one or more physical conditions.

75. The method of claim 74 wherein the monitoring of physical condition is related to non-medical purposes.

76. The method of claim 74 wherein the physical condition is related to a human being.

77. The method of claim 74 wherein the physical condition is related to an animal.

78. The method of claim 73 further comprising deriving geographic location of the physical condition.

79. The method of claim 78 wherein said code includes information about the accelerated state and geographic location.

80. The method of claim 73 wherein said pre-determined criteria is programmed into a processor at or near the physical location.

81. The method of claim 73 wherein said transmitted code is correlated to an event based on the comparison of actual transduced accelerated state to said pre-determined criteria.

82. The method of claim 73 wherein said transmitted code is correlated to continuing or future movements after the initial event, thereby showing possible degree of injury.

83. The method of claim 82 wherein an event is correlated to a status of the physical condition that is determined to require notification, treatment or response by a third party.

84. The method of claim 73 further comprising providing for a processing center adapted to communicate to and from the location of the physical condition.

85. The method of claim 84 wherein communication from the processing center comprises a request for status or communication check.

86. The method of claim 84 wherein the communication to the processing center comprises transmission of periodic status reports.

87. The method of claim 84 wherein an accelerated state is transduced from a plurality of persons.

88. The method of claim 87 wherein the plurality of persons are correlated to a set.

89. The method of claim 88 wherein the set is defined by a geographic region.

90. The method of claim 89 wherein the geographic region is taken from the set comprising the world, a portion of the world, a country, a portion of a country, and a subdivision of a portion of a country.

91. The method of claim 88 wherein the set is defined by authorized subscribers.

92. The method of claim 73 further comprising generating a response upon reception of a transmitted code.

93. The method of claim 92 wherein the response comprises calling a third party.

94. The method of claim 93 wherein the third party is selected from the set comprising ambulance company, doctor, fire department, police, EMT, neighbor, or employer.

95. The method of claim 92 wherein the response is an automatically generated signal.

96. The method of claim 92 wherein the response may be a radio signal.

97. The method of claim 92 wherein the response may be an audible sound signal.

98. The method of claim 73 further comprising a plurality of processing centers geographically distributed.

99. The method of claim 98 further comprising a plurality of wearable sensor/processors associated with subscribers to an authorized processing center.

100. A system for remote monitoring of the accelerated state for a plurality of users comprising:
    a wearable remote unit including an accelerometer, a device for determining geographic location, and wireless transceiver all operatively in communication with a processor;

a processing center including a wireless transceiver adapted for communication with the transceiver on the remote units;

pre-programmable parameters stored in the processor of each remote unit customized for the user of each remote unit;

software programmed in the processor of each remote unit adapted to compare a sensed acceleration with said customized parameters and causing transmission of a code to the processing center if indicated by the comparison, the code comprising information from which possible need of assistant in geographic location can be derived.

101. The system of claim 100 further comprising an output at the processing center which signals an indicated response action upon receipt of a code from a remote unit.

102. The system of claim 100 further comprising a geographic location device capable of calculating geographic location of the remote unit in operative connection with at least one of the processor and transmitter of the remote unit.

103. The system of claim 100 further comprising a manually operable alert which causes transmission of a code by the transmitter.

104. The system of claim 100 further comprising a component associated with the processing center adapted to generate status and/or location calls to any remote unit.

105. The system of claim 100 further comprising software at the processor of a remote unit adapted to periodically provide status and/or location reports to the processing center.

106. The system of claim 100 wherein said accelerometer of a remote unit is removable and substitutable.

107. The system of claim 100 wherein said acceleration is related to a medical condition of the user.

108. The system of claim 100 wherein the acceleration is related to a non-medical condition involving the user.

109. The system of claim 100 wherein the accelerometer is integrated with the processor and transmitter.

* * * * *

UNITED STATES PATENT AND TRADEMARK OFFICE
CERTIFICATE OF CORRECTION

PATENT NO. : 6,819,247 B2
DATED : November 16, 2004
INVENTOR(S) : Birnbach et al.

It is certified that error appears in the above-identified patent and that said Letters Patent is hereby corrected as shown below:

Column 13,
Line 9, should read:
-- selected from the set comprising: sending a query to the user, --

Column 14,
Line 51, should read:
-- or sensor; --

Column 17,
Line 12, should read:
-- which possible need of assistance in geographic location --

Signed and Sealed this

Twenty-second Day of February, 2005

JON W. DUDAS
*Director of the United States Patent and Trademark Office*